United States Patent [19]

Scholz

[11] 4,220,787
[45] Sep. 2, 1980

[54] PREPARATION OF OXAZOLIDINE-2,4-DIONES

[75] Inventor: Herbert Scholz, Ludwigshafen, Fed. Rep. of Germany

[73] Assignee: BASF Aktiengesellschaft, Fed. Rep. of Germany

[21] Appl. No.: 14,770

[22] Filed: Feb. 23, 1979

[30] Foreign Application Priority Data

Mar. 31, 1978 [DE] Fed. Rep. of Germany ....... 2813873

[51] Int. Cl.$^2$ .......................................... C07D 263/44
[52] U.S. Cl. .................................................. 548/226
[58] Field of Search ..................... 260/307 B; 548/226

[56] References Cited

U.S. PATENT DOCUMENTS 2,954,381  9/1960  Shapiro et al. ................... 260/307 B Primary Examiner—Jose Tovar
Attorney, Agent, or Firm—Keil & Witherspoon

[57] ABSTRACT

A process for the preparation of substituted oxazolidine-2,4-diones by treating a corresponding carbamate with a 2-hydroxycarboxylic acid ester at from 80° to 250° C.

2 Claims, No Drawings

PREPARATION OF OXAZOLIDINE-2,4-DIONES

The present invention relates to a novel process for the preparation of oxazolidine-2,4-diones by reaction of carbamates with 2-hydroxycarboxylic acid esters.

It is known to prepare oxazolidine-2,4-diones by reaction of isocyanates with 2-hydroxycarboxylic acid esters (German Published Application DAS No. 1,811,843, and German Laid-Open Applications DOS No. 2,022,494 and DOS No. 2,207,576).

I have found that an oxazolidone-2,4-dione of the formula

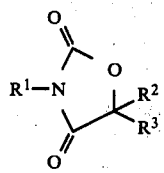

where $R^1$ is aryl of 6 to 12 carbon atoms which is unsubstituted or substituted by one or more halogen atoms, methyl or methoxy or is alkyl of 1 to 4 carbon atoms or allyl, $R^2$ is hydrogen or alkyl of 1 to 4 carbon atoms or vinyl, and $R^3$ has the same meanings as $R^2$, and $R^2$ and $R^3$ may be identical or different, is obtained in good yield and high purity when a carbamate of the formula

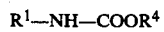

$$R^1-NH-COOR^4$$

where $R^1$ has the above meaning and $R^4$ is alkyl of 1 to 10 carbon atoms or cyclohexyl or aryl of 6 carbon atoms is reacted with a 2-hydroxycarboxylic acid ester of the formula

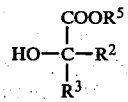

where $R^5$ has the same meanings as $R^4$, $R^4$ and $R^5$ may be identical or different and $R^2$ and $R^3$ have the above meanings, at from 80° to 250° C., in the presence or absence of a catalyst.

The following are examples of the meanings of the various substituents:

$R^1$: aryl, eg. phenyl, naphthyl, 2-, 3- and 4-fluorophenyl, 2-, 3- and 4-chlorophenyl, 2-, 3- and 4-bromophenyl, 2,3-dichlorophenyl, 2,3,6-trichlorophenyl, 2-, 3- and 4-methoxyphenyl, 2-, 3- amd 4-methylphenyl, 3,4-dichlorophenyl, 2,6-dichlorophenyl, 2,3,6-trichlorophenyl, 3,4,5-trichlorophenyl, 2,4,6-trichlorophenyl, 2,3,5-trichlorophenyl and preferably 3,5-dichlorophenyl, alkyl, eg. methyl, ethyl and isopropyl, and allyl.

$R^4$: alkyl, eg. methyl, isobutyl, butyl, propyl and ethyl, cyclohexyl and phenyl.

$R^2$: hydrogen, vinyl and alkyl, eg. methyl and ethyl.

The following meanings are preferred: $R^1 = 3,5$-dichlorophenyl, $R^4$ and $R^5 =$ isobutyl, methyl or butyl, $R^2 =$ methyl and $R^3 =$ vinyl.

The reaction must be carried out at an elevated temperature, viz. at from 80° to 250° C., preferably from 120° to 225° C. It is advantageous to carry out the reaction in the presence of a catalyst, because this makes it possible to use a lower reaction temperature.

Examples of catalysts used are halides, oxides and carboxylates of 1 to 12 carbon atoms of metals such as tin, lead, cobalt and copper. Specific examples are lead acetate, copper-II acetate, cobalt chloride, dibutyl-tin dilaurate and dibutyl-tin oxide.

Preferably, however, a tertiary organic amine is used as the catalyst, eg. trimethylamine, triethylamine, tripropylamine, tributylamine, tripentylamine, trihexylamine, triheptylamine, trioctylamine, trinonylamine, tridecylamine, dimethylcyclohexylamine and dimethylaniline.

The reaction can be carried out in the absence of a solvent; however, the addition of a solvent may be advantageous, especially if the latter forms an azeotrope with the alcohols $R^4OH$ and $R^5OH$ which must be distilled off, but does not form an azeotrope with the 2-hydroxycarboxylic acid ester starting material.

Examples of suitable solvents are xylene, benzene, α-pinene, methyl isobutyl ketone, isobutyl acetate, cyclohexane and, preferably, toluene.

Advantageously, stoichiometric amounts of the starting materials are used for the reaction. However, it is also possible to use an excess, for example of up to 10%, of one of the starting materials, advantageously of the cheaper starting material.

To achieve good conversion, it is important to remove the resulting alcohols $R^4OH$ and $R^5OH$ virtually quantitatively, preferably by distillation, and to ensure that the 2-hydroxycarboxylic acid ester used as the starting material does not distil at the same time. The use of packed distillation columns is particularly advantageous for this purpose.

The reaction can be carried out under normal pressure; reduced pressure, of from 65 to 950 mbar, can be of advantage in lowering the distillation temperature.

The carbamate used as the starting material is obtained by reacting an isocyanate with an alcohol or a carbamic acid chloride with an alcohol in the presence of an alkali, in the conventional manner. For example, reaction of 3,5-dichlorophenyl isocyanate with methyl alcohol gives methyl N-(3,5-dichlorophenyl)-carbamate (melting point 121° C.).

If, instead of methyl alcohol, isobutyl alcohol is used, isobutyl N-(3,5-dichlorophenyl)-carbamate (melting point 75° C.) is obtained. Methyl isocyanate and melting alcohol give methyl N-methylcarbamate.

The Examples which follow illustrate the process according to the invention.

EXAMPLE 1

132 parts by weight (0.6 mole) of methyl N-(3,5-dichlorophenyl)-carbamate (melting point 121° C.), 105.3 parts (0.6 mole) of 98% pure isobutyl vinyl-lactate and 5.6 parts (0.03 mole) of tributylamine are mixed. 38.4 parts of distillate (methanol and isobutanol) are distilled off through a 40 cm high distillation column (of 2 cm diameter, packed with wire gauze rings—2,400 meshes/cm²—made from stainless steel) in the course of 95 minutes at a pressure of 200 mbar, the mixture being at from 145° to 171° C. and the vapor at from 43° to 61.5° C. The residue is cooled to 90° C. (at which it remains liquid) and is added dropwise, whilst stirring, to 150 parts of methanol at 20° C. Stirring is continued for 2 hours at 20° C. and the solid which has separated out is filtered off and washed with twice 20 parts of methanol.

Yield: 150 parts of 3-(3,5-dichlorophenyl)-5-methyl-5-vinyl-1,3-oxazolidine-2,4-dione(Vinclozoline); this represents 88% yield). Melting point 106°-110° C.

EXAMPLE 2

159.2 parts (0.6 mole) of isobutyl N-(3,5-dichlorophenyl)-carbamate (melting point 75° C.), 105.3 parts (0.6 mole) of 98% pure isobutyl vinyl-lactate and 5.6 parts (0.03 mole) of tributylamine are refluxed for 1 hour. 73 parts by volume (=57.8 parts by weight) of distillate (isobutanol) are then distilled off through a distillation column (data as in Example 1) in the course of 5 hours, the mixture being at from 198° to 220° C. and the vapor at from 102° C. to 107° C. The residue is allowed to cool to 80° C. (it remains liquid) and is added dropwise to 150 parts of methanol at 20° C. Stirring is continued for 2 hours at 20° C. The Vinclozoline which has separated out is filtered off and dried.

Yield: 121 parts of Vinclozoline ≙ 70.5%. Melting point 105° C.

EXAMPLE 3

67 parts (0.76 mole) of methyl methylcarbamate, 114 parts by volume of toluene, 100 parts (0.76 mole) of ethyl 2-hydroxyisobutyrate and 28 parts (0.152 mole) of tributylamine are refluxed for 1 hour. Toluene, methanol and ethanol are then distilled off through a distillation column (data as in Example 1), the mixture being at from 155° to 190° C. and the vapor at from 79° to 90° C. The distillation residue is then fractionated at 10 mbar. At 87.5° C., 3-N-methyl-5,5-dimethyl-1,3-oxazolidin-2,4-dione passes over; the product crystallizes. Melting point 44° C.

Examples 4 to 10, below, were carried out similarly to Example 1, the reaction taking place according to the equation:

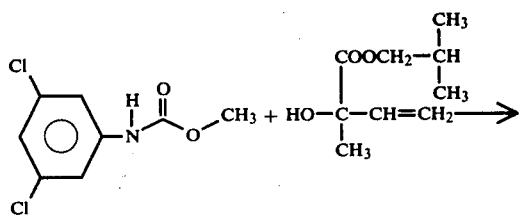

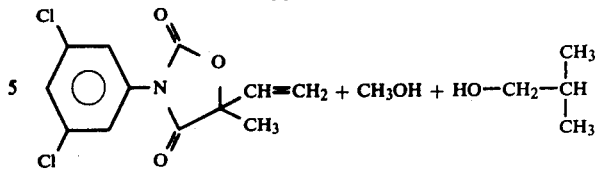

| Example No. | Batch size (mole) | Type of catalyst | Amount (mole) | Yield of Vinclozoline, % | Temperature of the mixture, °C. | Reaction time (hours) | Notes |
|---|---|---|---|---|---|---|---|
| 4 | 0.6 | Dibutyl-tin dilaurate | 0.06 | 93.5 | 160-190 | 2 | |
| 5 | 0.6 | None | — | 73 | 200-225 | 2 | |
| 6 | 0.6 | Copper-II acetate | 0.06 | 76 | 160-190 | 2 | Washed with water |
| 7 | 0.6 | Trioctylamine | 0.06 | 93.5 | 150-200 | 1 | |
| 8 | 0.6 | Cobalt-II chloride | 0.06 | 82.5 | 165-195 | 2 | |
| 9 | 0.6 | Lead-II-acetate | 0.06 | 91 | 160-200 | 1 | Washed with water |
| 10 | 0.6 | oxide | 0.06 | 88 | 135-185 | 3 | |

I claim:

1. A process for the preparation of an oxazolidine-2,4-dione of the formula

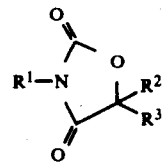

where $R^1$ is aryl of 6 to 12 carbon atoms which is unsubstituted or substituted by one or more halogen atoms, methyl or methoxy or is alkyl of 1 to 4 carbon atoms or allyl, $R^2$ is hydrogen or alkyl of 1 to 4 carbon atoms or vinyl, and $R^3$ has the same meanings as $R^2$, and $R^2$ and $R^3$ may be identical or different, which process comprises reacting a carbamate of the formula

where $R^1$ has the above meanings and $R^4$ is alkyl of 1 to 10 carbon atoms or cyclohexyl or aryl of 6 carbon atoms with a 2-hydroxycarboxylic acid ester of the formula

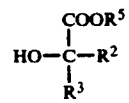

where $R^5$ has the same meanings as $R^4$, $R^4$ and $R^5$ may be identical or different and $R^2$ and $R^3$ have the above meanings, at from 80° to 250° C., in the presence or absence of a catalyst.

2. The process of claim 1, wherein $R^1$ is 3,5-dichlorophenyl, $R^2$ is methyl and $R^3$ is vinyl.

* * * * *